United States Patent [19]

Hong et al.

[11] 4,263,212
[45] Apr. 21, 1981

[54] PROCESS FOR PREPARATION OF SUBSTITUTED OLEFINS

[75] Inventors: Pangbu Hong, Tokyo; Hiroshi Yamazaki, Kamifukuoka, both of Japan

[73] Assignee: Rikagaku Kenkyusho, Wako, Japan

[21] Appl. No.: 121,313

[22] Filed: Feb. 14, 1980

[30] Foreign Application Priority Data

Feb. 28, 1979 [JP] Japan .................................. 54-23246
Oct. 16, 1979 [JP] Japan ................................. 54-133200

[51] Int. Cl.$^3$ ..................... C07G 27/00; C07C 2/66; C07C 307/36
[52] U.S. Cl. ........................... 260/347.5; 260/326.36; 260/326.44; 260/326.50; 260/326.5 FM; 260/346.74; 260/346.11; 260/347.3; 260/347.4; 260/347.8; 260/465 D; 260/465 F; 260/465 G; 260/465 H; 260/465 K; 542/454; 560/51; 560/53; 560/54; 560/55; 560/60; 560/81; 560/104; 562/459; 562/463; 562/465; 562/470; 562/489; 568/313; 568/315; 568/316; 568/317; 568/433; 568/626; 568/630; 568/631; 568/646; 568/654; 568/658; 568/659; 568/661; 568/662; 568/663; 585/438; 570/143

[58] Field of Search ..................... 260/326.36, 326.44, 260/326.5 D, 326.5 FM, 346.74, 346.11, 347.3, 347.4, 347.5, 347.8, 465 D, 465 F, 465 G, 465 H, 465 K, 649 R, 649 F, 650 R, 650 F; 542/454; 560/51, 53, 54, 55, 60, 81, 104; 562/459, 463, 465, 470, 489; 568/313, 315, 316, 317, 433, 626, 630, 631, 646, 654, 658, 659, 661, 662, 663; 585/438

[56] References Cited

U.S. PATENT DOCUMENTS

| | | | |
|---|---|---|---|
| 3,013,066 | 12/1961 | Alderson | 585/438 X |
| 3,499,007 | 3/1970 | von Brachel et al. | 260/346.74 |
| 3,775,511 | 11/1973 | Shue | 585/438 X |
| 3,859,311 | 1/1975 | Symon et al. | 560/104 X |

Primary Examiner—Richard Raymond
Attorney, Agent, or Firm—Bucknam and Archer

[57] ABSTRACT

The present invention relates to a process for the preparation of aromatic or furyl substituted olefins, which comprises reacting an olefinic compound with an aromatic compound or furan compound in the presence of carbon monoxide by using a rhodium carbonyl complex as a catalyst to form a corresponding aromatic or furyl substituted olefin.

9 Claims, No Drawings

PROCESS FOR PREPARATION OF SUBSTITUTED OLEFINS

BACKGROUND OF THE INVENTION (1) Field of the Invention:

The present invention relates to a process for the preparation of aromatic or furyl substituted olefins, which comprises reacting an olefinic compound with an aromatic compound or furan compound in the presence of carbon monoxide by using a rhodium carbonyl complex as a catalyst to form a corresponding aromatic or furyl substituted olefin.

(2) Description of the Prior Art:

Aromatic substituted olefinic hydrocarbons represented by styrene have heretofore been industrially prepared according to the process comprising reacting an olefin with an aromatic hydrocarbon in the presence of a Friedel-Crafts catalyst to form an aromatic substituted hydrocarbon, and then dehydrogenating the so formed aromatic substituted hydrocarbon. Needless to say, great industrial advantages would be attained if an aromatic substituted olefin could be prepared directly from an olefin and an aromatic hydrocarbon without adopting this two stage process.

It is known that a palladium salt is effective for such a direct preparation process. This process using a palladium salt catalyst, however, is defective in that the reduced palladium is precipitated and the yield of the product per unit amount of the catalyst is low. Various attempts have been made to improve reaction conditions or catalysts, for example, by adding a promotor represented by an oxidant for controlling precipitation of palladium (see, for example, Japanese Patent Publication No. 14496/76). However, satisfactory results can hardly be obtained by these attempts. Furthermore, olefins applied to this reaction using a palladium salt as a catalyst are limited to those having a relatively simple structure, such as ethylene and styrene, and olefins having a functional group have hardly been applied to this reaction and if applied, the yield are very low (see I. Moritani and Y. Fujiwara, Synthesis, 524 (1973)).

It is known that an alkenylfuran can be obtained if furan is reacted with an olefinic compound in the presence of a palladium salt catalyst. For example, when furan is reacted with methyl acrylate or acrylonitrile, methyl (2-furyl)acrylate or (2-furyl)acrylonitrile is synthesized (see O. Maruyama, Y. Fujiwara and H. Taniguchi, Preprints II, 3L 14, The 37th Annual Meeting of The Chemical Society of Japan, April, 1978).

This process for synthesizing alkenyl substituted furan compounds by direct reaction between furan and olefinic compounds has attracted attention in the art, because the reaction course in this process is greatly shortened as compared with the reaction course in the conventional process requiring numerous steps. This process, however, is still defective in that applicable furan compounds and olefinic compounds are limited to specific compounds and the yield per unit amount of the catalyst is very low.

CROSS-REFERENCE TO RELATED APPLICATIONS

We previously proposed a process comprising adding an aromatic hydrocarbon to a cumulene compound such as a ketone or isocyanate and an acetylenic compound in the presence of carbon monoxide by using a rhodium carbonyl catalyst to prepare a corresponding aromatic compound (see the specifications of Japanese Patent Applications No. 24159/78 and No. 24160/78). We furthered research on the activity of the rhodium carbonyl catalyst to various compounds and found that aromatic or furyl substituted olefins can be obtained in good yields directly from olefinic compounds and aromatic compounds or furan compounds.

SUMMARY OF THE INVENTION

The present invention relates to a process in which an olefinic compound which may or may not have a substituent is reacted with an aromatic which may or may not have a substituent or a furan compound which may or may not have a substituent in the presence of carbon monoxide by using a rhodium carbonyl complex as a catalyst, whereby a corresponding aromatic or furyl substituted olefin is directly obtained.

This process is expressed by the following reaction formula:

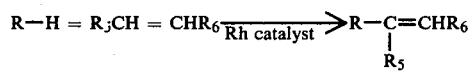

wherein R stands for

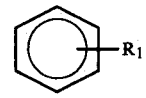

(in which $R_1$ stands for a hydrogen atom, an alkyl group having 1 to 4 carbon atoms, an alkoxy group having 1 to 4 carbon atoms, a methoxycarbonyl group, an acetoxy group, a cyano group or a halogen atom, two or more of which substituents may be present and if so, they may be the same or different), or

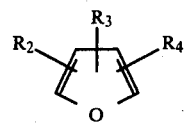

in which $R_2$, $R_3$ and $R_4$, which may be the same or different, stand for a hydrogen atom, an alkyl group having 1 to 4 carbon atoms, a phenyl group, an acetyl group, a formyl group or a methoxycarbonyl group, and $R_5$ and $R_6$, which may be the same or different, stand for a hydrogen atom, an alkyl group having 1 to 4 carbon atoms, an aryl group, an alkoxy group having 1 to 4 carbon atoms, an acyl group, a carboxyl group, an alkoxycarbonyl group having 1 to 4 carbon atoms, a formyl group or a cyano group, or $R_5$ and $R_6$ may be bonded together to form a group

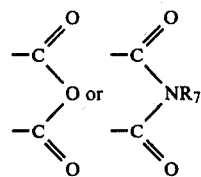

in which $R_7$ stands for a hydrogen atom, an alkyl group having 1 to 4 carbon atoms or a phenyl group.

DETAILED DESCRIPTION OF THE PREFERRED EMBODIMENTS

As the olefinic compound ($R_5CH=CHR_6$) that is used in the present invention for reaction with an aromatic compound or furan compound, there can be mentioned, for example, olefinic hydrocarbons such as ethylene, aryl substituted olefinic hydrocarbons such as styrene, and olefinic compounds having a functional group linked to the olefin bond, such as acrolein, crotonaldehyde, vinylalkyl ketones, acrylic acid, acrylic acid esters, crotonic acid, crotonic acid esters, fumaric acid, fumaric acid esters, maleic acid, maleic acid esters, maleic anhydride, maleimide and N-substituted maleimides.

As the aromatic compound that is used in the present invention, there can be mentioned, for example, benzene and substituted aromatic compounds, e.g., mono-substituted benzenes such as toluene, ethylbenzene, propylbenzene, butylbenzene, anisole, ethoxybenzene, butoxybenzene, fluorobenzene, methyl benzoate, acetoxybenzene and benzonitrile and substituted benzenes having at least 2 substituents, such as xylene, ethyltoluene, methylanisole, ethylanisole, dimethoxybenzene and diethoxybenzene.

The furan compound that is used in the present invention includes unsubstituted furan and substituted furans having 1 to 3 substituents selected from alkyl groups having 1 to 4 carbon atoms and aryl, alkoxycarbonyl, acyl and formyl groups. As specific examples of such substituted furan, there can be mentioned alkyl furans such as 2-methylfuran, 2-ethylfuran and 2,5-dimethylfuran, and 2-(methoxycarbonyl)furan, 2-acetylfuran and furfural.

When an aromatic compound or furan compound such as mentioned above is heated together with an olefinic compound such as mentioned above in the presence of carbon monoxide by using a rhodium carbonyl complex as a catalyst, an aromatic or furyl substituted olefin can be prepared. For example, styrene can be obtained in a high yield from benzene and ethylene, and when an acrylic acid ester, vinylmethyl ketone, maleic anhydride and an N-substituted maleimide are used instead of ethylene, it is possible to obtain a cinnamic acid ester, benzalacetone, phenylmaleic anhydride and phenylmaleimide, respectively. When a fumaric acid ester or malic acid ester is used, a mixture of a phenylfumaric acid ester and a phenylmaleic acid ester is obtained in each case.

When furan is similarly reacted with an olefin, the reaction advances regio-selectively and a (2-furyl) olefin is obtained. For example, when furan is reacted with ethylene, an acrylic acid ester and vinylmethyl ketone, it is possible to obtain (2-furyl)ethylene, a (2-furyl)acrylic acid ester and 4-(2-furyl)buten-3-on-2, respectively.

When a substituted benzene is used in the process of the present invention, a product is obtained in the form of a mixture of positional isomers. Since the reactivity and orientation of the substituted benzene in the reaction of the process of the present invention differ from those in the conventional electrophilic substitution reaction (see P. Hong, H. Yamazaki, K. Sonogashira and N. Hagihara, Chemistry Letters, 535 (1978)), substituted aromatic compounds that cannot be easily synthesized according to the conventional techniques can be prepared selectively and easily according to the process of the present invention. For example, in the present invention, a vinyltoluene mixture is prepared from toluene and ethylene, and the ortho/meta/para isomer ratio in this mixture is 14/57/29, with the meta-isomer as a main product. Furthermore, when fluorobenzene and anisole are reacted with ethylene, the ortho/meta/para isomer ratios in the resulting isomer mixtures are 67/23/10 and 78/17/5, respectively, and in each case, the ortho-styrene derivative is obtained as a main product.

If such differences in the reactivity and orientation among substituents are appropriately utilized, an alkenyl group can be selectively introduced into a poly-substituted aromatic compound having different substituents. For example, when p-methoxytoluene is used, the ortho-position to the methoxy group is preferentially substituted by an alkenyl group.

On the other hand, when a 2-substituted furan compound is used, the reaction occurs preferentially on the 5-position. More specifically, when 2-methylfuran, 2-acetylfuran, 2-(methoxycarbonyl)furan or furfural is reacted with methyl methacrylate, a product in which the vinyl group is introduced selectively in the 5-th position is obtained. This shows that the $\alpha$-position has a very high reactivity. However, in case of a furan compound in which both the $\alpha$-positions are blocked by substituents, for example, 2,5-dimethylfuran, reaction takes place even on the $\beta$-position and a (3-2,5-dimethylfuryl)acrylic acid ester is obtained.

In the reaction of the present invention, as illustrated in Examples given hereinafter, for example, in the reaction of benzene or furan with ethylene, diethyl ketone is formed as a by-product simultaneously with formation of styrene or vinylfuran. It is considered that hydrogen produced at the formation of styrene or vinylfuran participates in such side reaction. In some cases, this hydrogen reduces the starting compound and reaction product. For example, when an acrylic acid ester, maleic anhydride or an N-substituted maleimide is used, a part of the starting compound is reduced, and when fumaric acid, a maleic acid ester or vinylmethyl ketone is used, parts of the starting compound and product are reduced.

When the starting aromatic or furan compound is liquid, this may also be used as a reaction solvent, or it may be diluted with a solvent such as hexane, tetrahydrofuran, dioxane or ethyl acetate. Since the reactivity of benzene is lower than that of a furan compound, benzene can be used as the solvent when a furan compound is reacted. The use of such solvent is advantageous in that it is possible to reduce the amount of the aromatic compound or furan compound used.

When acetylfuran or furfural is used singly, a considerable amount of a product by self-condensation is formed, but if the reactant is diluted with a solvent such as mentioned above and the reaction is carried out, self-condensation is inhibited and the intended product can be isolated with ease.

In the present invention, rhodium complexes composed mainly of a rhodium carbonyl compound, such as $Rh_4(CO)_{12}$, $Rh_6(CO)_{16}$, $Rh_2(CO)_4Cl_2$, $Rh(CO)_2(CH_3COCHCOCH_3)$ and $(CH_3COORh(CO)_2)_2$, are preferably employed as catalysts. Furthermore, rhodium complexes that can be converted in the presence carbon monoxide to rhodium carbonyl compounds, such as $Rh_2(1,5\text{-cyclooctadiene})_2Cl_2$ and $Rh(1,5\text{-cyclooctadiene})-(NC_5H_5)Cl$, can also be used as catalysts.

In the present invention, the molar ratio of the reactants is not particularly critical. Ordinarily, the molar ratio of the aromatic compound or furan compound to the olefinic compound is about 1 to about 100, preferably about 10 to about 50. In the present invention, the rhodium complex catalyst is used in an amount of about 0.001 to about 0.1 mole, preferably about 0.005 to about 0.01 mole, as rhodium atom per mole of the olefinic compound.

In the present invention, it is important that the reaction be carried out in the presence of carbon monoxide. The presence of carbon monoxide prevents decomposition of the catalyst which will occur with advance of the reaction and functions to maintain the activity of the catalyst for a long time.

Palladium catalysts are often regenerated by oxygen under an elevated pressure. Since a mixture comprising oxygen and an olefinic compound such as ethylene is explosive, such regeneration method involves a risk. In contrast, the present invention involves no such risk at all.

In the process of the present invention, the reaction is ordinarily carried out at about 150° to about 300° C. and it is preferred that the reaction be carried out at about 180° to about 250° C., especially about 220° to about 250° C.

The reaction time is ordinarily within a range of from about 1 to about 20 hours, and it is preferred that the reaction be carried out for about 5 to about 10 hours, especially about 6 to about 8 hours. The partial pressure of carbon monoxide is not particularly critical in the present invention, but ordinarily, the partial pressure of carbon monoxide is adjusted to about 10 to about 40 kg/cm$^2$, preferably about 20 to about 30 kg/cm$^2$.

Aromatic substituted olefins represented by styrene derivatives and furyl substituted olefins, which are obtained according to the present invention, are valuable as monomers or as starting compounds for use in manufacture of perfumes, plasticizers, synthetic resins, dyes, medicines and agricultural chemicals.

The present invention will now be described in detail with reference to the following Examples that by no means limit the scope of the present invention.

EXAMPLE 1

Charged in an autoclave having an inner capacity of 200 ml were 50 ml of benzene and 0.019 g of Rh$_4$(CO)$_{12}$, followed by supply of ethylene under 30 kg/cm$^2$ and carbon monoxide under 25 kg/cm$^2$. The charge in the autoclave was heated at 250° C. for 7 hours while shaking. The reaction mixture was cooled and analyzed by a gas chromatograph (hereinafter referred to as "GC"), and it was confirmed that 1.227 g of styrene was formed. The yield of styrene was 11800% based on the Rh atom. In addition to styrene, 1.739 of diethylketone was formed as a by-product. The diethylketone was converted into a 2,4-dinitrohydrazone derivative and identified by comparison with the standard substance. Furthermore, formation of 40 mg of trans-stilbene was confirmed.

EXAMPLE 2

Charged in an autoclave having an inner capacity of 200 ml were 50 ml of benzene and 0.019 g of Rh$_6$(CO)$_{16}$, followed by supply of ethylene under 30 kg/cm$^2$ and carbon monoxide under 25 kg/cm$^2$. The charge in the autoclave was heated at 220° C. under agitation for 7 hours. The reaction mixture was cooled and analyzed by GC and it was confirmed that 0.925 g of styrene was formed. The yield of styrene was 8900% based on the Rh atom. Furthermore, it was confirmed that 1.129 g of diethylketone and 40 mg of trans-stilbene were formed.

EXAMPLE 3

The reaction and analysis were carried out in the same manner as described in Example 2 except that 0.040 g of Rh$_2$(CO)$_4$Cl$_2$ was used instead of Rh$_6$(CO)$_{16}$, and 0.30 g of styrene was obtained. The yield of styrene was 1450% based on the Rh atom. Furthermore, it was confirmed that 0.10 g of diethylketone was formed.

EXAMPLE 4

The reaction and analysis were carried out in the same manner as described in Example 2 except that 0.025 g of Rh(CO)$_2$(CH$_3$COCHCOCH$_3$) was used instead of Rh$_6$(CO)$_{16}$. It was confirmed that 0.666 g of styrene and 0.778 g of diethylketone were formed. The yield of styrene was 6400% based on the Rh atom.

EXAMPLE 5

In the same autoclave as used in Example 1, 50 ml of toluene and 0.019 g of Rh$_4$(CO)$_{12}$ were charged, followed by supply of ethylene under 30 kg/cm$^2$ and carbon monoxide under 20 kg/cm$^2$. The charge in the autoclave was heated at 220° C. under agitation for 18 hours. The reaction mixture was cooled and analyzed by GC. It was confirmed that 0.741 of vinyltoluene was formed, and the yield of the vinyltoluene was 6280% based on the Rh atom. In the so formed vinyltoluene, the ortho/meta/para isomer ratio was 14/57/29.

EXAMPLE 6

The reaction was carried out in the same manner as described in Example 5 except that 50 ml of anisole was used instead of toluene and the heating time was changed to 7 hours. By GC, it was confirmed that 1.451 g of vinylanisole was formed. The yield of vinylanisole was 10830% based on the Rh atom. In the formed vinylanisole, the ortho/meta/para isomer ratio was 67/23/10.

EXAMPLE 7

The reaction and analysis were carried out in the same manner as described in Example 5 except that 25 g of fluorobenzene and 10 mg of Rh$_4$(CO)$_{12}$ were used. It was confirmed that 0.507 g of a vinyl-fluorobenzene isomer mixture (ortho/meta/para isomer ratio=78/17/5) was formed and the yield was 8320% based on the Rh atom.

EXAMPLE 8

The reaction was carried out in the same manner as in Example 5 except that 30 ml of p-xylene was used instead of toluene. By the GC analysis of the reaction mixture, it was confirmed that 0.119 g of vinylxylene and 0.212 g of diethylketone were formed.

EXAMPLE 9

The reaction was carried out in the same manner as in Example 5 except that 50 ml of t-butylbenzene was used instead of toluene, and by the GC analysis of the reaction mixture, it was confirmed that 0.545 g of vinyl-t-butylbenzene and 0.62 g of diethylketone were formed.

EXAMPLE 10

In the same autoclave as used in Example 1, 50 ml of benzene, 0.98 g of maleic anhydride and 0.019 g of Rh$_4$(CO)$_{12}$ were charged, followed by supply of carbon monoxide under 30 kg/cm². The charge in the autoclave was heated at 220° C. for 7 hours. The reaction mixture was cooled and benzene was removed by distillation under reduced pressure. The residue was separated by silica column chromatography to obtain 0.363 g of phenylmaleic anhydride and 0.136 g of succinic anhydride. Each product was identified based on the infrared absorption spectrum (hereinafter referred to as "IR") of the standard substance and the retention time in GC.

EXAMPLE 11

The reaction and post treatment were carried out in the same manner as described in Example 10 except that 1.73 g of N-phenylmaleimide was used instead of maleic anhydrate, to obtain 0.566 g of N-phenyl phenylmaleimide and 0.762 g of N-phenyl succinimide. At this reaction, 0.221 g of the starting material was recovered. The formed N-phenyl phenylmaleimide was identified by elementary analysis, IR spectrum and nuclear magnetic responance spectrum (hereinafter referred to as "NMR").

EXAMPLE 12

Charged in the same autoclave as used in Example 1, were 1.78 g of methyl acrylate, 50 ml of benzene and 0.019 g of $Rh_4(CO)_{12}$, followed by supply of carbon monoxide under 30 kg/cm². The charge in the autoclave was heated at 220° C. for 8 hours. The reaction mixture was cooled and analyzed by GC, and formation of 0.762 g of methyl cinnamate was confirmed. The yield of methyl cinnamate was 4700% based on the Rh atom. The so formed methyl cinnamate was in agreement with a commercially available product of methyl cinnamate with respect to the IR spectrum and the retention time in GC.

EXAMPLE 13

The reaction and post treatment were carried out in the same manner as described in Example 12 except that 50 ml of methyl benzoate was used instead of 50 ml of benzene, to obtain 0.660 g of a methyl (methoxycarbonyl)cinnamate isomer mixture (ortho/meta/para isomer ratio=20/45/35). The yield was 3000% based on the Rh atom.

EXAMPLE 14

The reaction and post treatment was carried out in the same manner as described in Example 12 except that 50 ml of acetoxybenzene was used instead of 50 ml of benzene, to obtain 0.77 g of a methyl (acetoxy)cinnamate isomer mixture (ortho/meta/para isomer ratio=57/30/13). The yield was 3500% based on the Rh atom.

EXAMPLE 15

The reaction and post treatment were carried out in the same manner as described in Example 12 except that 50 ml of benzonitrile was used instead of 50 ml of benzene, to obtain 0.320 g of a methyl cyanocinnamate isomer mixture (ortho/meta/para isomer ratio=22/47/31). The yield was 1700% based on the Rh atom.

EXAMPLE 16

Charged in an autoclave having an inner capacity of 200 ml, were 16.32 g (209 millimoles) of benzene, 1.745 g (20.26 millimoles) of methyl acrylate and 19.4 mg (0.026 millimole) of $Rh_4(CO)_{12}$, followed by supply of 60 ml of ethyl acetate. Carbon monoxide under 30 kg/cm² was introduced into the autoclave and reaction was carried out at 220° C. for 6 hours to obtain 0.197 g (1.22 millimoles) of methyl cinnamate. The yield of methyl cinnamate was 6% based on methyl acrylate and 1170% based on the Rh atom.

EXAMPLE 17

The reaction and post treatment were carried out in the same manner as described in Example 16 except that 60 ml of hexane was used instead of 60 ml of ethyl acetate, to obtain 0.108 g (0.67 millimole) of methyl cinnamate. The yield was 3% based on methyl acrylate and 640% based on the Rh atom.

EXAMPLE 18

The reaction and analysis were carried out in the same manner as described in Example 12 except that 1.4 g of vinylmethyl ketone was used instead of methyl acrylate and the reaction time and temperature were adjusted to 7 hours and 220° C., respectively. It was confirmed that 0.433 g of benzalacetone and 0.167 g of benzylacetone were formed. The yields of benzalacetone and benzylacetone were 2970% and 1130%, respectively, based on the Rh atom. Identification of the products was performed by comparison with the standard substances with respect to the retention time in GC.

EXAMPLE 19

The reaction and analysis were carried out in the same manner as described in Example 18 except that 1.44 g of dimethyl maleate was used instead of vinylmethyl ketone and the reaction time was changed to 6 hours. Formation of 0.324 g of dimethyl phenylmaleate, 0.161 g of dimethyl phenylfumarate and 0.147 g of dimethyl phenylsuccinate was confirmed. Furthermore, formation of 0.261 g of dimethyl succinate and 0.357 g of dimethyl fumarate was confirmed. Each product was in agreement with the standard product synthesized separately, with respect to the IR and NMR spectra and the retention time in GC.

EXAMPLE 20

The reaction and analysis were carried out in the same manner as described in Example 19 except that 1 g of dimethyl fumarate was used instead of dimethyl maleate, to obtain 0.232 g of dimethyl phenylmaleate, 0.114 g of dimethyl phenylfumarate, 0.108 g of dimethyl phenylsuccinate and 0.211 g of dimethyl succinate.

EXAMPLE 21

Charged in a shaking type stainless steel autoclave having an inner capacity of 100 ml, were 30 ml of furan, 1.083 g of methyl acrylate and 0.04 g of $Rh_4(CO)_{12}$, followed by supply of carbon monoxide under 25 kg/cm². Reaction was carried out at 220° C. for 7 hours. After completion of the reaction, the obtained reddish orange reaction solution was concentrated under reduced pressure and separated and purified by silica gel column chromatography. From a fraction eluted with benzene/hexane (3/2 to 4/1) was obtained 0.74 g of methyl $\beta$-(2-furyl)acrylate (1) (the yield was 39% based on methyl acrylate).

The structure of the product was confirmed by comparison with the standard substance with respect to the IR spectrum and NMR spectrum and also by comparison of β-(2-furyl)acrylic acid formed by saponification of the product with the standard substance with respect to the melting point and IR spectrum.

The formation of 0.358 g of methyl propionate was confirmed by the GC analysis of the reaction solution.

EXAMPLE 22

The reaction and post treatment were carried out in the same manner as described in Example 21 except that 30 ml of 2-methylfuran was used instead of 30 ml of furan, the amount of methyl acrylate was changed to 1.015 g and the reaction temperature was changed to 200° C. From a fraction eluted with benzene/hexane (4/1) was obtained 0.51 g of methyl β-(5-methyl-2-furyl)acrylate (2) (the yield was 26%).
(Physical Properties of Product (2))
Melting point: 36°–37° C. (colorless crystal).
NMR Spectrum (100 MHz, CDCl$_3$, δ(ppm): 7.33 (d, J=16 Hz, =CH), 6.48 (d, J=3 Hz, H$_4$), 6.19 (d, J=16 Hz, =CH), 6.05 (d, J=3 Hz, H$_3$), 3.76 (s, O-CH$_3$), 2.32 (s, CH$_3$).

Formation of 0.363 g of methyl propionate was confirmed by the GC analysis of the reaction solution.

EXAMPLE 23

Charged in a stainless steel autoclave having an inner capacity of 200 ml were 5.5 g of 2-acetylfuran, 1.72 g of methyl acrylate, 0.038 g of Rh$_4$(CO)$_{12}$ and 50 ml of tetrahydrofuran, followed by supply of carbon monoxide under 30 kg/cm$^2$. Reaction was carried out at 220° C. for 7 hours. Tetrahydrofuran and unreacted 2-acetylfuran were removed from the obtained light brown solution by distillation under reduced pressure, and the residue was separated and purified by silica gel column chromatography. From a fraction eluted with methylene chloride was obtained 0.62 g of methyl β-(5-acetyl-2-furyl)acrylate (3) (the yield was 16%).
(Physical Properties of Product (3))
Melting Point: 135°–136° C. (colorless crystal).
NMR Spectrum (100 MHz, CDCl$_3$, δ(ppm)): 7.42 (d, J=16 Hz), 7.17 (d, J=4 Hz), 6.69 (d, J=4 Hz), 6.52 (d, J=16 Hz), 3.79 (s, O—CH$_3$), 2.49 (s, COCH$_3$).

EXAMPLE 24

The reaction was carried out in the same manner as described in Example 23 except that 11 g of 2-acetylfuran, 1.84 g of methyl acrylate, 0.034 g of Rh$_6$(CO)$_{16}$ and 39 g of benzene were used and the reaction temperature and reaction time were changed to 240° C. and 5 hours, respectively. By the GC analysis of the reaction solution, formation of 0.789 g of methyl β-(5-acetyl-2-furyl)acrylate (3) and 0.402 g of methyl cinnamate was confirmed.

EXAMPLE 25

The reaction was carried out in the same manner as described in Example 21 except that 25 ml of 2-(methoxycarbonyl)furan and 0.939 g of methyl acrylate were used. Unreacted 2-(methoxycarbonyl)furan was removed from the obtained reaction solution by distillation under reduced pressure. Recrystallization of the solid residue gave 0.65 g of methyl β-(5-methoxycarbonyl-2-furyl)acrylate (4) (the yield was 28%).
(Physical Properties of Product (4))
Melting Point: 142°–143.5° C. (colorless crystal).
NMR Spectrum (100 MHz, CDCl$_3$, δ(ppm)): 7.41 (d, J=16 Hz, =CH), 7.16 (d, J=4 Hz, H$_4$), 6.65 (d, J=4 Hz), 6.52 (d, J=16 Hz, =CH), 3.88 (s, OCH$_3$), 3.77 (s, OCH$_3$).

EXAMPLE 26

The reaction was carried out in the same manner as described in Example 21 except that 1.01 g of vinylmethyl ketone, 30 ml of furan and 0.054 g of Rh$_6$(CO)$_{16}$ were used. Formation of 0.211 g of 4-(2-furyl)buten-3-on-2 (5) (the yield was 11%), 0.211 g of 4-(2-furyl)-butanone-2 (6) (the yield was 11%) and 0.069 g of 4,4-bis(2-furyl)butanone-2 (7) (the yield was 2%) was confirmed by the GC analysis of the reaction solution.

These products were separated and isolated by gas chromatography and their structures were estimated from the results of the NMR spectrum analysis. Finally, they were converted to 2,4-dinitrophenylhydrazone derivatives and identification was performed by the mass spectrum and elementary analysis.
(Physical Properties of Product (5))
State:
Colorless oil
NMR Spectrum (100 MHz, CDCl$_3$, δ (ppm): 7.48 (d, J=2 Hz, H$_5$), 7.27 (d, J=15 Hz, =CH), 6.66 (dd, J=2 Hz, J=4 Hz, H$_4$), 6.47 (d, J=4 Hz, H$_3$), 5.97 (d, J=15 Hz, =CH), 2.31 (s, CH$_3$)
(Physical Properties of 2,4-Dinitrophenylhydrazone Derivative of Product (5))
Melting Point: 230°–232° C. (reddish orange crystal).
Mass Spectrum: M+ 316 (molecular weight=316).
(Physical Properties of Product (6))
State:
Colorless oil
NMR Spectrum (100 MHz, CDCl$_3$, δ (ppm): 7.25 (d, J=2 Hz, H$_5$), 6.26 (dd, J=2 Hz, J=4 Hz, H$_4$), 5.96 (d, J=4 Hz, H$_3$), 2.83 (m, —CH$_2$CH$_2$—), 2.13 (s, CH$_3$).
(Physical Properties of 2,4-Dinitrophenylhydrazone Derivative of Product (6))
Melting Point: 116.5°–118° C. (yellowish orange crystal).
Mass Spectrum: M+ 318 (molecular weight=318).
(Physical Properties of Product (7))
State:
Colorless oil
NMR Spectrum (100 MHz, CDCl$_3$, δ (ppm)): 7.27 (d, J=2 Hz, H$_5$), 6.25 (dd, J=2 Hz, J=4 Hz, H$_4$), 6.03 (d, J=4 Hz, H$_3$), 4.71 (t, J=7 Hz, >CH—), 3.12 (d, J=7 Hz, —CH$_2$—), 2.11 (s, CH$_3$)
(Physical Properties of 2,4-Dinitrophenylhydrazone Derivative of Product (7))
Melting Point: 146°–149° C. (orange crystal).
Mass Spectrum: M+ 384 (molecular weight=384).

EXAMPLE 27

The reaction and post treatment were carried out in the same manner as described in Example 21 except that 2.16 g of dimethyl fumarate was used instead of methyl acrylate.

Unreacted dimethyl fumarate (0.666 g) was removed by elution with benzene/hexane (3/1), and 0.425 g of a colorless oil composed of a mixture comprising dimethyl (2-furyl)succinate (8) and dimethyl (2-furyl)-maleate (9) at a ratio of about 3/1 was obtained from a fraction eluted with benzene/methylene chloride (4/1 to 1/1). Formation of the products was confirmed by NMR.
(Physical Properties of Product (8))
NMR Spectrum (100 MHz, CDCl$_3$, δ (ppm): 7.31 (d, J=2 Hz, H$_5$), 6.30 (dd, J=2 Hz, J=4 Hz, H$_4$), 6.16 (d, J=4 Hz, H$_3$), 4.23 (dd, JHaHc=6 Hz, JHbHc=9 Hz, HC), 3.68 (s, O—CH$_3$), 3.64 (s, O—CH$_3$), 3.16 (dd, JHaHc=9 Hz, JHaHb=17 Hz), 2.76 (dd, JHaHc=6 Hz, JHaHb=17 Hz)

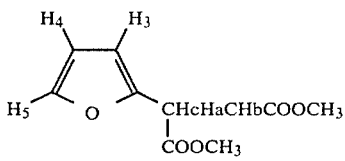

(Physical Properties of Product (9))

NMR Spectrum (100 MHz, CDCl₃, δ (ppm)): 7.50 (d, J=2 Hz, H₅), 6.57 (d, J=4 Hz, H₃), 6.46 (dd, J=2 Hz, J=4 Hz, H₄), 6.31 (s, =CH), 3.92 (s, O—CH₃), 3.76 (s, O—CH₃).

EXAMPLE 28

The reaction was carried out in the same manner as described in Example 21 except that 2.177 g of dimethyl maleate, 30 ml of furan and 0.038 g of Rh₆(CO)₁₆ were used and the reaction time was adjusted to 8 hours. Formation of 0.210 g of dimethyl (2-furyl)succinate (the yield was 6%), 0.066 g of dimethyl (2-furyl)maleate (the yield was 2%) and 0.387 g of dimethyl succinate (the yield was 18%) was confirmed by the GC analysis. Furthermore, formation of 1.305 g of dimethyl fumarate, an isomer of dimethyl maleate (the yield was 53%), was confirmed.

EXAMPLE 29 charged in an autoclave were 6.8 g of furan, 0.019 g of Rh₄(CO)₁₂ and 50 ml of tetrahydrofuran, followed by supply of ethylene under 30 kg/cm² and carbon monoxide under 25 kg/cm². The charge in the autoclave was heated at 220° C. for 7 hours. Formation of 0.581 g of (2-furyl)ethylene and 1.651 g of diethyl ketone was confirmed by the GC analysis of the reaction mixture.

What we claim is:

1. A process for the preparation of substituted olefins, which comprises reacting an aromatic or furan compound represented by the following general formula:

R—H wherein R stands for

(in which R₁ stands for a hydrogen atom, an alkyl group having 1 to 4 carbon atoms, an alkoxy group having 1 to 4 carbon atoms, a methoxycarbonyl group, an acetoxy group, a cyano group or a halogen atom, two or more of which substituents may be present and, if so, they may be the same or different), or

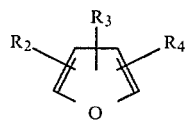

wherein R₂, R₃ and R₄, which may be the same or different, stand for a hydrogen atom, an alkyl grup having 1 to 4 carbon atoms, a phenyl group, an acetyl group, a formyl group or a methoxycarbonyl group, with an olefinic compound represented by the following general formula:

R₅CH=CHR₆ wherein R₅ and R₆, which may be the same or different, stand for a hydrogen atom, an alkyl group having 1 to 4 carbon atoms, an aryl group, an alkoxy group having 1 to 4 carbon atoms, an acyl group, a carboxyl group, an alkoxycarbonyl group having 1 to 4 carbon atoms, a formyl group or a cyano group, or R₅ and R₆ may be bonded together to form a group

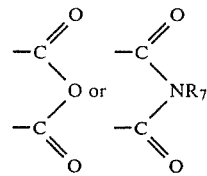

in which R₇ stands for a hydrogen atom, an alkyl group having 1 to 4 carbon atoms or a phenyl grup, in the presence of carbon monoxide by using a rhodium carbonyl complex as a catalyst, to form a substituted olefin represented by the following general formula:

R—CR₅=CHR₆ wherein R, R₅ and R₆ are as defined above.

2. A process for the preparation of substituted olefins according to claim 1, wherein the aromatic compound is selected from the group consisting of benzene, toluene, ethylbenzene, propylbenzene, butylbenzene, anisole, ethoxybenzene, butoxybenzene, fluorobenzene, methyl benzoate, acetoxybenzene, benzonitrile, xylene, ethyltoluene, methylanisole, ethylanisole, dimethoxybenzene and diethoxybenzene.

3. A process for the preparation of substituted olefins according to claim 1, wherein the furan compound is selected from the group consisting of furan, 2-methylfuran, 2-ethylfuran, 3,5-dimethylfuran, 2-(methoxycarbonyl)furan, 2-acetylfuran and furfural.

4. A process for the preparation of substituted olefins according to claim 1, wherein the olefinic compound is selected from the group consisting of ethylene, styrene, acrolein, crotonaldehyde, vinylalkyl ketone, acrylic acid, acrylic acid esters, crotonic acid, crotonic acid esters, fumaric acid, fumaric acid esters, maleic acid, maleic acid esters, maleic anhydride, maleimide and N-substituted maleimides.

5. A process for the preparation of substituted olefins according to claim 1, wherein the rhodium carbonyl complex is selected from the group consisting of Rh₄(CO)₁₂, Rh₆(CO)₁₆, Rh₂(CO)₄Cl₂, Rh(CO)₂(CH₃COCHCOCH₃), (CH₃COORh(CO)₂)₂, Rh(1,5-cyclooctadine)(NC₅H₅)Cl and Rh₂(1,5-cyclooctadiene)₂Cl₂.

6. A process for the preparation of substituted olefins according to claim 1, wherein the pressure of carbon monoxide is about 10 and about 40 kg/cm².

7. A process for the preparation of substituted olefins according to claim 1, wherein the reaction temperature is about 180° to about 250° C.

8. A process for the preparation of substituted olefins according to claim 2, wherein the reaction is carried out in a reaction solvent selected from the group consisting of hexane, tetrahydrofuran, dioxane and ethyl acetate.

9. A process for the preparation of substituted olefins according to claim 3, wherein the reaction is carried out in a reaction solvent selected from the group consisting of hexane, tetrahydrofuran, dioxane, ethyl acetate and benzene.

* * * * *